United States Patent
Takahashi

(10) Patent No.: US 8,409,106 B2
(45) Date of Patent: Apr. 2, 2013

(54) BLOOD PRESSURE MEASUREMENT DEVICE FOR MEASURING BLOOD PRESSURE WITH CLOTHES ON

(75) Inventor: Akihisa Takahashi, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 666 days.

(21) Appl. No.: 12/532,936

(22) PCT Filed: Apr. 9, 2008

(86) PCT No.: PCT/JP2008/057018
§ 371 (c)(1),
(2), (4) Date: Sep. 24, 2009

(87) PCT Pub. No.: WO2008/133012
PCT Pub. Date: Nov. 6, 2008

(65) Prior Publication Data
US 2010/0063406 A1  Mar. 11, 2010

(30) Foreign Application Priority Data
Apr. 24, 2007 (JP) .................. 2007-114436

(51) Int. Cl.
*A61B 5/0225* (2006.01)

(52) U.S. Cl. .............. 600/494; 600/485; 600/493

(58) Field of Classification Search ........... 600/490–499
See application file for complete search history.

(56) References Cited

U.S. PATENT DOCUMENTS
| | | | |
|---|---|---|---|
| 3,654,915 A * | 4/1972 | Sanctuary | 600/495 |
| 5,103,830 A * | 4/1992 | Shinomiya | 600/485 |
| 7,232,412 B2 | 6/2007 | Shirasaki et al. | |

FOREIGN PATENT DOCUMENTS
| | | |
|---|---|---|
| JP | 2602466 B2 | 7/2000 |
| JP | 2004-180910 A | 7/2004 |

OTHER PUBLICATIONS

Ahmed, Iftekhar, et al. "Measuring the Blood Pressure Do We Really Need Sleeves Rolled Up?." Pakistan Heart Journal 39.3-4 (2006).*
Ma, Grace, Norman Sabin, and Martin Dawes. "A comparison of blood pressure measurement over a sleeved arm versus a bare arm." Canadian Medical Association Journal 178.5 (2008): 585-589.*
Kahan, Ernesto, et al. "Comparison of blood pressure measurements on the bare arm, below a rolled-up sleeve, or over a sleeve." Family practice 20.6 (2003): 730-732.*
International Search Report w/translation from PCT/JP2008/057018 dated May 18, 2008 (2 pages).
Patent Abstracts of Japan; Publication No. 06-294126 dated Oct. 21, 1994; Kajima Corp. (1 page).
Patent Abstracts of Japan; Publication No. 2004-180910 dated Jul. 2, 2004; Omron Healthcare Co. Ltd. (1 page). Mizuta, F. et al.; "Chakui ya Udemakuri ga Oscillometric-shiki Ketsuatsukei no Sokuteichi ni Ataeru Eikyo" (translated as "Effect of clothes and sleeved arms on oscillometric blood pressure measurement"); University Dental Journal, vol. 24, No. 1; Jun. 2005; pp. 24-30 (7 pages).

* cited by examiner

*Primary Examiner* — Patricia Mallari
*Assistant Examiner* — Michael Catina
(74) *Attorney, Agent, or Firm* — Osha Liang LLP

(57) ABSTRACT

A sphygmomanometer (1) stores a parameter for calculating a blood pressure value from a measurement value with clothes on from a measurement value with clothes off at a measurement site and the measurement value with clothes on in advance. When a with-clothes mode is selected with a button (3-4) in measuring the blood pressure, the blood pressure value is calculated using the parameter stored with respect to the measurement value.

8 Claims, 14 Drawing Sheets

BLOOD PRESSURE MEASUREMENT DEVICE FOR MEASURING BLOOD PRESSURE WITH CLOTHES ON

TECHNICAL FIELD

The present invention relates to a blood pressure measurement device, a measurement data processing method, and a measurement data processing program product, in particular, to an oscillometric blood pressure measurement device, a method of processing measurement data measured with the oscillometric blood pressure measurement device, and a program product for causing a computer to process.

BACKGROUND ART

In an oscillometric blood pressure measurement device as disclosed in Japanese Unexamined Patent Publication No. 2004-180910 (hereinafter referred to as Patent Document 1), a blood pressure of a measurer is measured by wrapping and fixing an armband (cuff) internally including an air bag to a predetermined site of a living body or the measurer, and measuring a change in internal pressure or a change from an initial state of the internal pressure by pressurizing and depressurizing the air bag.

FIG. 14 is a view describing a determination method of a blood pressure value in an oscillometric method. A portion (A) of FIG. 14 is a view showing a specific example of a change between a cuff pressure and an artery blood pressure and a relationship between the cuff pressure and the artery blood pressure involved with elapse of time with pressure on a vertical axis and time on a horizontal axis. In the portion (A) of FIG. 14, a curve A1 shows the change of the artery blood pressure, and a line segment (or curve) A2 shows the change of the cuff pressure. In this case, the cuff internal pressure is pressurized to a predetermined pressure at an initial stage, and then gradually depressurized at a constant depressurization speed in the next stage to perform blood pressure measurement in the depressurization stage. When determining the blood pressure value with reference to the portion (A) of FIG. 14, the measurement result from a time point (first time point) at which the cuff pressure corresponds to the maximum pressure (cardiac systolic blood pressure) of the artery blood pressure in the depressurization stage to a time point (second time point) at which the cuff pressure corresponds to the minimum pressure (cardiac diastolic blood pressure) of the artery blood pressure is used.

The portion (B) of FIG. 14 shows a curve (envelope curve) showing a change of an amplitude of the artery blood pressure wave with respect to the cuff pressure from the first time point to the second time point with a pressure pulse wave amplitude on a vertical axis and the cuff pressure on a horizontal axis. In the oscillometric method, the blood pressure value is determined using the envelope curve in the calculation.

In the conventional blood pressure measurement device as disclosed in Patent Document 1, the blood pressure is generally measured with clothes off or with sleeves rolled up. However, taking the clothes off or rolling up the sleeves in an area where the temperature is particularly low is a strong irritation to the body of the measurer, and becomes a cause of blood pressure fluctuation. Taking into consideration that the measurer who needs to have the blood pressure measured is often elderly, causing sudden irritation in the body of the measurer is preferably avoided as much as possible. In addition, an upper part of an upper arm is strongly compressed by rolling up the sleeves, to no small extent, and the influence on the blood pressure cannot be ignored. Thus, there is a demand to measure the blood pressure with clothes on. If the measurement can be carried out with the clothes on, the merit on the user side in that measurement can be more easily carried out is large.

Patent Document 1: Japanese Unexamined Patent Publication No. 2004-180910

DISCLOSURE OF THE INVENTION

Problems to be Solved by the Invention

When a blood pressure is measured with clothes on, a curve (envelope curve) showing a change of amplitude of an artery blood pressure wave with respect to a cuff pressure becomes as shown in a portion (C) of FIG. 14. The portion (C) of FIG. 14 shows a curve (envelope curve) showing the change of the amplitude of the artery blood pressure wave with respect to the cuff pressure from the first time point to the second time point in the case where the blood pressure is measured with clothes on with amplitude on the vertical axis and cuff pressure on the horizontal axis.

When the blood pressure is measured with clothes on with reference to the portion (C) of FIG. 14, the beat of the pulse is absorbed by the clothes, which is between the cuff and the measurement site. The amplitude value becomes smaller than the amplitude value without the clothes shown at the portion (B) of FIG. 14. As a result, the shape of the envelope curve changes from the shape of the envelope curve shown at the portion (B) of FIG. 14. This means that the compression force of the cuff is lost or that loss occurs in the propagation of the pulse beat to the cuff by having the clothes between the cuff and the measurement site.

In other words, in the conventional blood pressure measurement device as disclosed in Patent Document 1, the loss of the beat of the pulse or the compression force of the cuff may occur due to the clothes and the measurement accuracy may not be ensured if the blood pressure is measured with clothes on.

In view of such problems, it is an object of the present invention to provide a blood pressure measurement device a measurement data processing method, and a measurement data processing program product capable of enhancing the measurement accuracy when the blood pressure is measured with clothes on in the oscillometric blood pressure measurement method.

Means for Solving the Problems

In order to achieve the above-mentioned objects, in accordance with one aspect of the present invention, a blood pressure measurement device includes: a measurement fluid bag; a sensor for measuring a change in inner pressure of the measurement fluid bag; a first setting unit for setting a parameter in correspondence to information related to clothes of a measurement site in time of measurement of a person to be measured; and a calculation unit for calculating a blood pressure value using the parameter based on the change in inner pressure of the measurement fluid bag obtained by the sensor.

In accordance with another aspect of the present invention, there is provided a processing method in a computer of measurement data obtained by a blood pressure measurement device including a measurement fluid bag and a sensor for measuring a change in inner pressure of the measurement fluid bag, the method including the steps of: setting a parameter in correspondence to information related to clothes of a measurement site in time of measurement of a person to be measured; and calculating a blood pressure value using the parameter based on the change in inner pressure of the measurement fluid bag obtained by the sensor.

In accordance with still another aspect of the present invention, there is provided a program product for causing a computer to execute a process of measurement data obtained by a blood pressure measurement device including a measurement fluid bag and a sensor for measuring a change in inner pressure of the measurement fluid bag, the measurement data processing program product causing the computer to execute the steps of: setting a parameter in correspondence to information related to clothes of a measurement site in time of measurement of a person to be measured; and calculating a blood pressure value using the parameter based on the change in inner pressure of the measurement fluid bag obtained by the sensor.

Effect of the Invention

According to the present invention, measurement accuracy in the case where a blood pressure is measured with clothes on can be enhanced.

Figure 1:
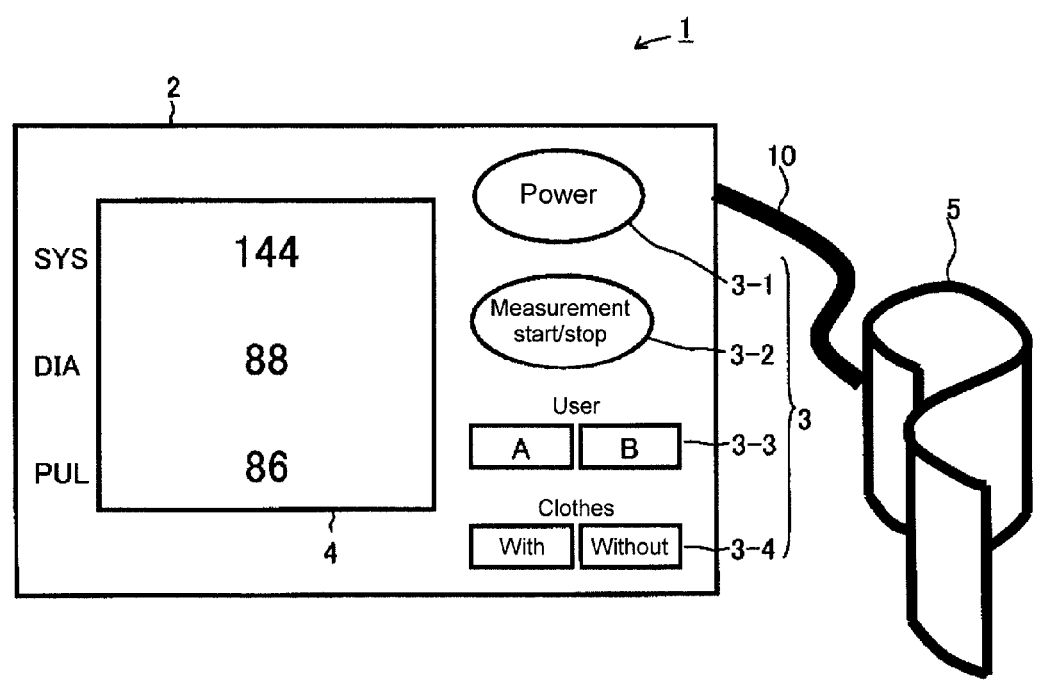
FIG. 1 is a schematic view of an outer appearance of a sphygmomanometer according to a first embodiment of a blood pressure measurement device.

DESCRIPTION OF THE REFERENCE NUMERALS 1, 1' Sphygmomanometer
2 Main body
3 Operation unit
3-1 to 3-5 Button
4 Display unit
5 Armband
10 Air tube
13 Measurement air bag
20 Measurement air system
21 Pump
22 Valve
23 Pressure sensor
26 Pump drive circuit
27 Valve drive circuit
28 Amplifier
29 A/D converter
40 CPU
41 Memory unit
101 Mode selecting unit
103 Measurement result input unit
105 Measurement result storage unit
107 First judgment unit
109 Reference value storage unit
111 Parameter determination unit
113 Parameter storage unit
115 Annunciation unit
121 Parameter acquiring unit
123 Second judgment unit
125 Calculation unit

BEST MODE FOR CARRYING OUT THE INVENTION

Embodiments of the present invention will be described below with reference to the drawings. In the following description, same reference numerals are denoted for the same parts and components. Names and functions thereof are the same.

[First Embodiment]

With reference to FIG. 1, a sphygmomanometer 1 according to a first embodiment of a blood pressure measurement device includes a main body 2 and an armband 5 to be wrapped around an upper arm or a measurement site, and the main body 2 and the armband 5 are connected with an air tube 10. An operation unit 3 such as buttons and a display unit 4 for displaying measurement results and the like are arranged on a front surface of the main body 2.

The operation unit 3 includes a button 3-1, a button 3-2, a button 3-3, and a button 3-4. The button 3-1 is used to instruct ON/OFF of the power. The button 3-2 is used to instruct start/stop of the measurement. The button 3-3 is used to select a user. The button 3-4 is used to select whether to measure with clothes on or to measure with clothes off as information related to clothes in time of the measurement of a person to be measured.

The armband 5 is arranged with a measurement air bag 13 (see FIG. 2), where the measurement air bag 13 is pressed against the measurement site by wrapping the armband 5 around the upper arm or the measurement site.

Figure 2:
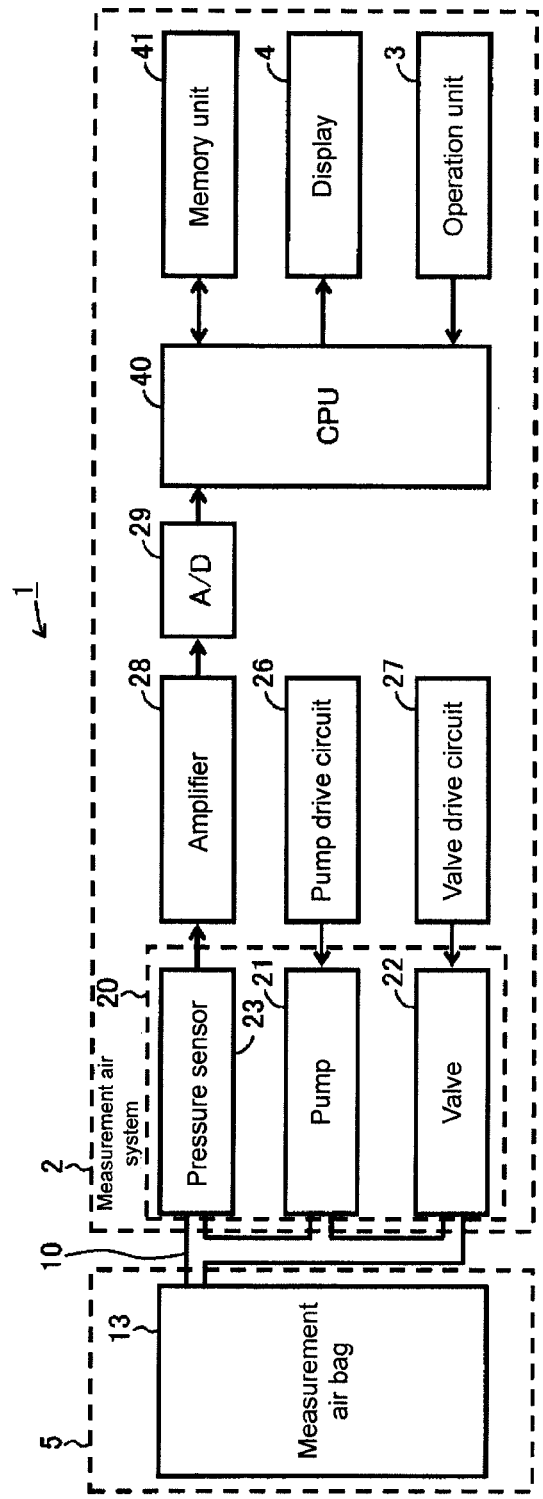
FIG. 2 is a block diagram showing a specific example of a hardware configuration of the sphygmomanometer according to the first embodiment.

With reference to FIG. 2, the measurement air bag 13 is connected to a measurement air system 20. The measurement air system 20 includes a pressure sensor 23, a pump 21 for supplying/exhausting air, and a valve 22. The pressure sensor 23 measures an internal pressure change of the measurement air bag 13. The pump 21 supplies/exhausts air to the measurement air bag 13.

The main body 2 of the sphygmomanometer 1 includes a CPU (Central Processing Unit) 40, an amplifier 28, a pump drive circuit 26, a valve drive circuit 27, an A/D (Analog to Digital) converter 29, and a memory unit 41. The CPU 40 controls the entire sphygmomanometer 1. The amplifier 28, the pump drive circuit 26, and the valve drive circuit 27 are connected to the measurement air system 20. The A/D converter 29 is connected to the amplifier 28. The memory unit 41 stores programs executed by the CPU 40 and the measurement results.

The CPU 40 executes a predetermined program stored in the memory unit 41 based on an operation signal inputted from the operation unit 3, and outputs a control signal to the pump drive circuit 26 and the valve drive circuit 27. The pump drive circuit 26 and the valve drive circuit 27 drive the pump 21 and the valve 22 according to the control signal to execute the blood pressure measurement operation.

The pressure sensor 23 detects the internal pressure change of the measurement air bag 13, and inputs a detection signal to the amplifier 28. The inputted pressure signal is amplified to a predetermined amplitude in the amplifier 28, converted to a digital signal in the A/D converter 29, and then inputted to the CPU 40. The CPU 40 executes a predetermined process based on the internal pressure change of the measurement air bag 13 obtained from the pressure sensor 23, and outputs the control signal to the pump drive circuit 26 and the valve drive circuit 27 according to the result. The CPU 40 also calculates a blood pressure value based on the internal pressure change of the measurement air bag 13 obtained from the pressure sensor 23, and outputs the measurement result to display on the display unit 4.

Opening and closing of the valve 22 are controlled by the valve drive circuit 27 following the control signal from the CPU 40 to exhaust air in the measurement air bag 13.

Figure 3:
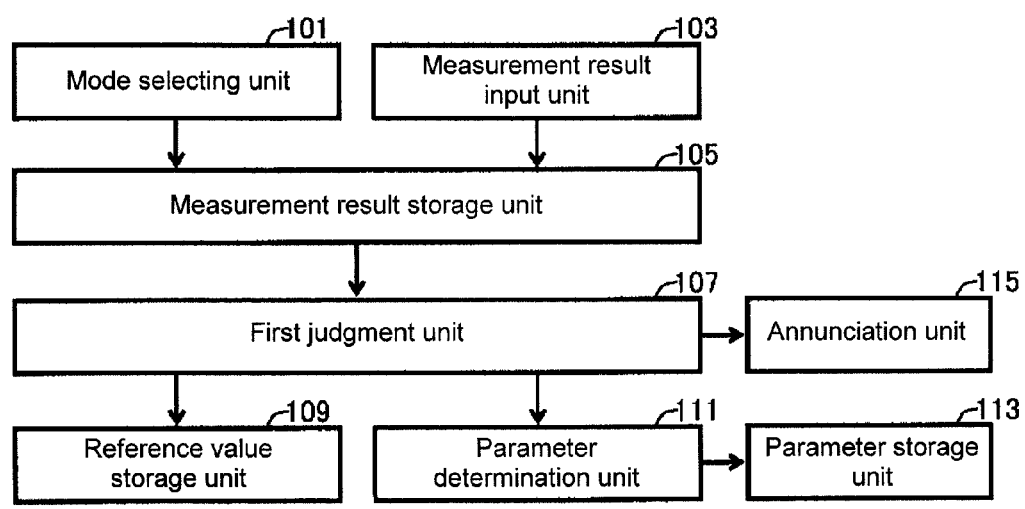
FIG. 3 is a block diagram showing a specific example of a function configuration for performing a registration process in the sphygmomanometer according to the first embodiment.

In the sphygmomanometer 1, a registration process for registering values and parameters necessary for calculating the blood pressure value when clothes is worn is performed prior to the measurement. Each function for performing the registration process in the sphygmomanometer 1 shown in FIG. 3 is the function mainly provided in the CPU 40 when the CPU 40 executes a predetermined program stored in the memory unit 41. Some of the functions shown in FIG. 3 may be provided by other configurations of the CPU 40 shown in FIG. 2.

With reference to FIG. 3, a function for performing the registration process in the sphygmomanometer 1 is configured to include a mode selecting unit 101, a measurement result input unit 103, a measurement result storage unit 105, a first judgment unit 107, a reference value storage unit 109, a parameter determination unit 111, a parameter storage unit 113, and an annunciation unit 115.

The mode selecting unit 101 accepts the input of the operation signal by the operation of the button 3-4, selects whether the blood pressure measurement mode is a mode with clothes on or a mode without clothes from the measurement site, and inputs a signal indicating the selection result to the measurement result storage unit 105. In the following description, the former mode is referred to as "with-clothes mode" and the latter mode is referred to as "without-clothes mode".

The measurement result input unit 103 accepts the input of the measurement result from the pressure sensor 23 through the amplifier 28 and the A/D converter 29, and stores the same in the measurement result storage unit 105. The measurement result storage unit 105 stores the measurement result accepted in the measurement result input unit 103 in correspondence to the measurement mode inputted by the mode selecting unit 101. In the registration process, the measurement is assumed to be performed a plurality of times, for example, three times for each mode, and the measurement result storage unit 105 stores the three inputted measurement results in correspondence to the mode thereof for the with-clothes mode and the without-clothes mode.

The first judgment unit 107 reads out the measurement result in the with-clothes mode and the measurement result in the without-clothes mode stored in the measurement result storage unit 105, and judges whether or not the measurement result is appropriate. If the measurement result is appropriate, the first judgment unit 107 inputs the measurement result to the reference value storage unit 109 and the parameter determination unit 111. If the measurement result is not appropriate, the first judgment unit 107 inputs a signal indicating such to the annunciation unit 115. The annunciation unit 115 generates a signal for displaying a warning on the display unit 4, and inputs the same to the display unit 4. If a warning lamp or the like representing the same is arranged in the sphygmomanometer 1, the annunciation unit 115 may output a control signal for lighting the warning lamp. If warning is made through other methods, the process corresponding to such a method may be performed in the annunciation unit 115.

Figure 4:
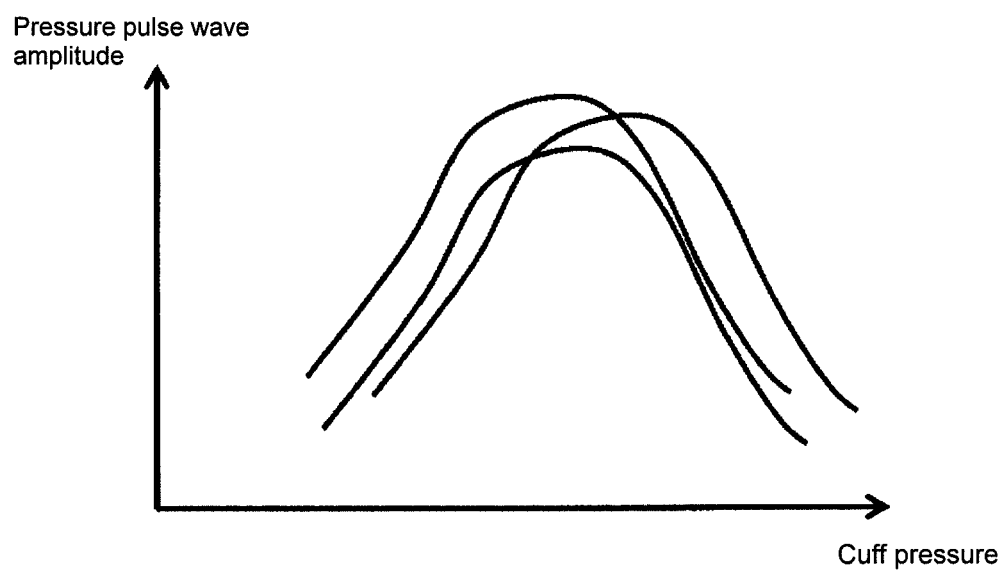
FIG. 4 is a view showing a specific example of a curve showing a change of amplitude of an artery blood pressure wave with respect to the cuff pressure.

The first judgment unit 107 calculates variation of the measurement result and judges whether it is within a predetermined range in each mode as a first judgment. The method of calculating the variation of the measurement result is not limited to a specific method in the present invention, and various methods may be adopted. For instance, if the curve (envelope curve) showing a change of the amplitude of the artery blood pressure wave with respect to the cuff pressure obtained in the three measurements in a certain mode has relationship shown in FIG. 4, the first judgment unit 107 judges that the variation is large in the first judgment, and inputs a signal indicating the judgment result to the annunciation unit 115. If the variation of the measurement result is large in the measurement under the same condition (with/without clothes), the influence of clothes in the with-clothes modes is difficult to be accurately grasped with respect to the measurement result in the without-clothes mode. Whether or not an effective measurement result is obtained in the blood pressure measurement of the plurality of times in each mode is judged by the first judgment in the first judgment unit 107.

The first judgment unit 107 judges whether or not the relationship between the measurement result in the with-clothes mode and the measurement result in the without-clothes mode is appropriate as a second judgment and a third judgment. In this case, the average value of a plurality of measurement results in each mode may be used as the measurement result of the relevant mode, a representative measurement result may be used as the measurement result of the relevant mode, or other calculation values may be used as the measurement result of the relevant mode.

Figure 5:
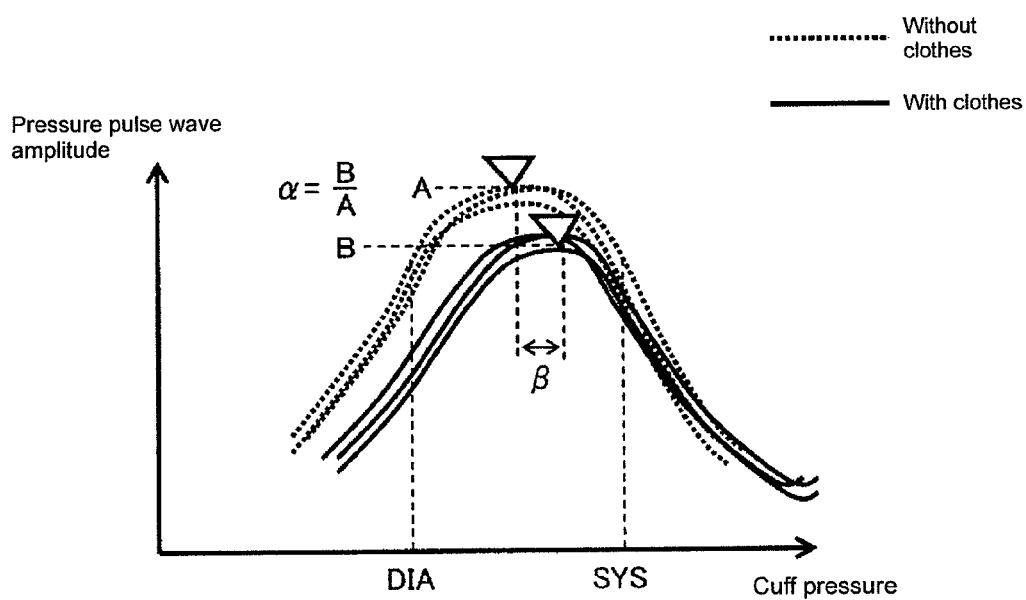
FIG. 5 is a view showing a specific example of a curve showing a change of amplitude of the artery blood pressure wave with respect to the cuff pressure in a with-clothes mode and a without-clothes mode.

Specifically, the first judgment unit 107 judges whether or not a ratio (B/A) of an amplitude (B) of the envelope curve in the with-clothes mode with respect to an amplitude (A) of the envelope curve in the without-clothes mode is greater than or equal to a threshold value α as the second judgment, as shown in FIG. 5. The first judgment unit 107 also judges whether or not a transition of the cuff pressure at the peak of the envelope curve in the without-clothes mode with respect to the cuff pressure at the peak of the envelope curve in the with-clothes mode is smaller than or equal to a threshold value β as the third judgment. The first judgment unit 107 inputs a signal indicating the result of the third judgment to the annunciation unit 115.

Figure 6:
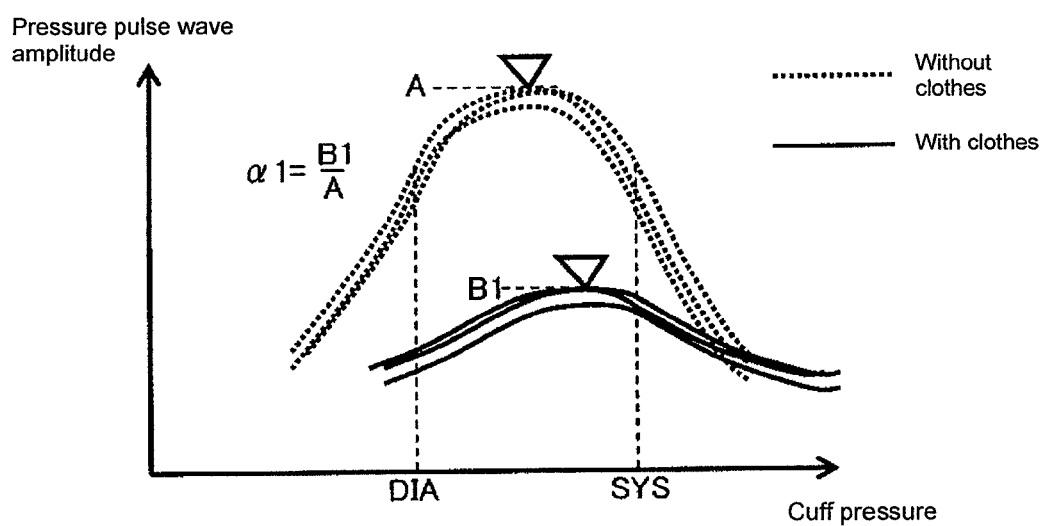
FIG. 6 is a view showing a specific example of a curve showing a change of amplitude of the artery blood pressure wave with respect to the cuff pressure in the with-clothes mode and the without-clothes mode.

Assume the relationship between the envelope curve in the with-clothes mode and the envelope curve in the without-clothes mode is the relationship shown in FIG. 6. In FIG. 6, a ratio α1 (=B1/A) of an amplitude (B1) of the envelope curve in the with-clothes mode with respect to the amplitude of the envelope curve in the without-clothes mode (A) is greater than or equal to the threshold value α. In this case, the first judgment unit 107 judges that the relationship between the measurement result in the with-clothes mode and the measurement result in the without-clothes mode is not appropriate as the second judgment. If the above ratio of the amplitudes is greater than or equal to the threshold value, this means that the influence of clothes on the measurement result is greater than the correctable range in the with-clothes mode and that the blood pressure measurement in the with-clothes mode is not appropriate. Thus, it is judged by the second judgment in the first judgment unit 107 whether or not the pulse beat that is lost by being absorbed by clothes when the measurement is performed with clothes on is in the correctable range.

Figure 7:
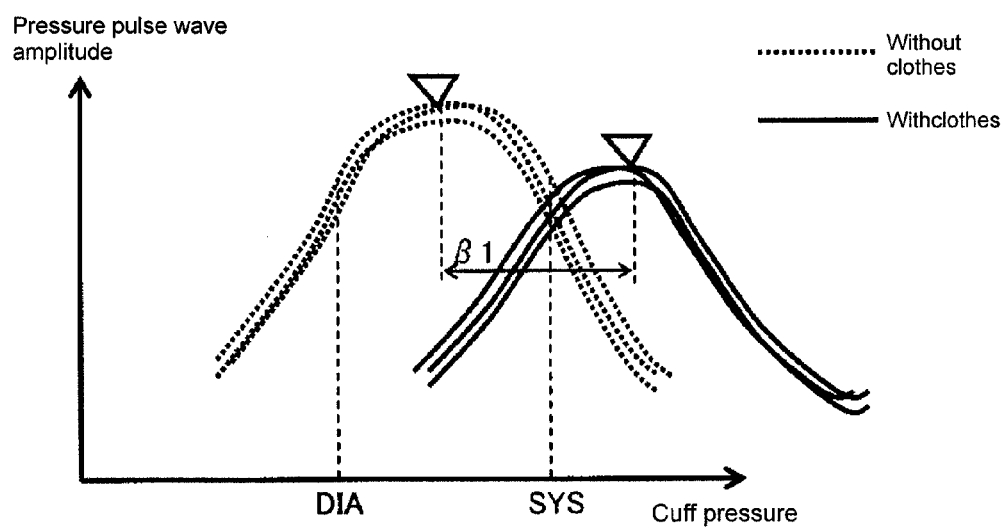
FIG. 7 is a view showing a specific example of a curve showing a change of amplitude of the artery blood pressure wave with respect to the cuff pressure in the with-clothes mode and the without-clothes mode.

Assume the relationship between the envelope curve in the with-clothes mode and the envelope curve in the without-clothes mode is the relationship shown in FIG. 7. In FIG. 7, the transition β1 of the cuff pressure at the peak of the envelope curve in the without-clothes mode with respect to the cuff pressure at the peak of the envelope curve in the with-clothes mode is greater than or equal to the threshold value β. In this case, the first judgment unit 107 judges that the relationship between the measurement result in the with-clothes mode and the measurement result in the without-clothes mode is not appropriate as the third judgment. The first judgment unit 107 then inputs the signal indicating the judgment result to the annunciation unit 115. If the above transition is greater than or equal to the threshold value, this means that the influence of clothes on the measurement result is greater than the correctable range in the with-clothes mode and that the blood pressure measurement in the with-clothes mode is not appropriate. Thus, it is judged by the third judgment in the first judgment unit 107 whether or not the compression force by the cuff that is lost by being absorbed by clothes when the measurement is performed with clothes on is in the measurable range.

If judged that the measurement result is appropriate in all the judgments of the first judgment, the second judgment, and the third judgment, the first judgment unit 107 stores in the reference value storage unit 109 the amplitude value of the artery blood pressure wave and the shape of the envelope curve obtained from the measurement result in the with-clothes mode as a reference value in the with-clothes mode.

The parameter determination unit 111 determines the ratio α1 of the amplitude, the transition β1 of the cuff pressure at the peak, or the value calculated from α, β as parameters necessary for calculating the blood pressure value when the clothes is worn when judged that the measurement result is appropriate in all of the judgments of the above first judgment, the second judgment, and the third judgment in the first judgment unit 107, and stores the same in the parameter storage unit 113.

Figure 8:
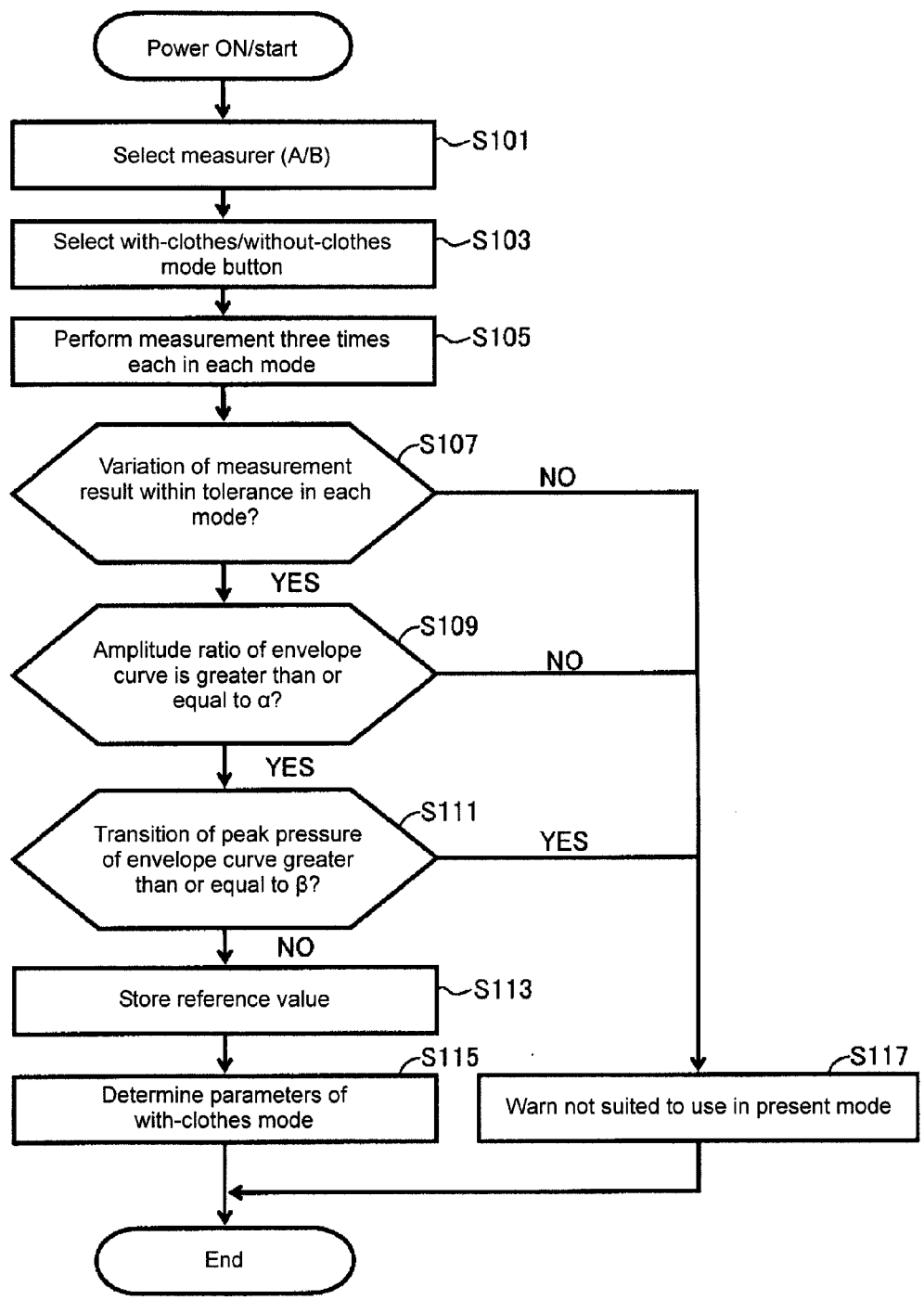
FIG. 8 is a flowchart showing a specific example of a flow of a registration process in the sphygmomanometer according to the first embodiment.

The registration process in the sphygmomanometer 1 shown in the flowchart of FIG. 8 starts when the button 3-1 is pushed and the power is turned ON. The process of FIG. 8 is realized by causing the CPU 40 to read out and execute a predetermined program stored in the memory unit 41 to exhibit the functions shown in FIG. 3. The process of FIG. 8 may start when a button (not shown) for starting the registration process is pushed or when a predetermined operation for starting the registration process is performed.

With reference to FIG. 8, the CPU 40 accepts an operation signal for selecting the measurer (A or B) by the operation of the button 3-3 (step S101), and determines the measurer. The CPU 40 then accepts the operation signal for selecting the with-clothes mode or the without-clothes mode by the operation of the button 3-4 and selects the mode in the mode selecting unit 101 (step S103).

When the selection of the mode is accepted in step S103, the blood pressure value is measured over a plurality of times in each accepted mode (step S105). As a specific example, the measurement is carried out three times each in each mode.

With respect to the measurement result of step S105, the first judgment unit 107 performs the first judgment (step S107) on whether or not the variation of the measurement result is within a tolerance level in each mode, the second judgment (step S109) on whether or not the ratio of the amplitude of the envelope curve in the without-clothes mode with respect to the amplitude of the envelope curve in the with-clothes mode is greater than or equal to the threshold value, and the third judgment (step S111) on whether or not the transition of the cuff pressure at the peak of the envelope curve in the without-clothes mode with respect to the cuff pressure at the peak of the envelope curve in the with-clothes mode is greater than or equal to the threshold value.

If judged that all conditions are satisfied in the first judgment to the third judgment (YES in step S107, YES in S109, and NO in S111), the amplitude value of the artery blood pressure wave and the shape of the envelope curve obtained from the measurement result in the with-clothes mode are stored in the reference value storage unit 109 as a reference value in the with-clothes mode (step S113). Furthermore, the ratio α1 of the amplitude, the transition β1 of the cuff pressure at the peak, or the value calculated from the threshold values obtained in steps S109 and S111 are determined, in the parameter determination unit 111, as parameters necessary for calculating the blood pressure value when the clothes is worn (step S115), and are stored in the parameter storage unit 113.

If judged that one of the conditions is not satisfied in the first judgment to the third judgment (NO in step S109, NO in S109, or YES in S111), the annunciation unit 115 executes a process of annunciating that the blood pressure measurement in the with-clothes mode is not appropriate, and outputs a warning (step S117).

The registration process in the sphygmomanometer 1 is then terminated.

Figure 9:
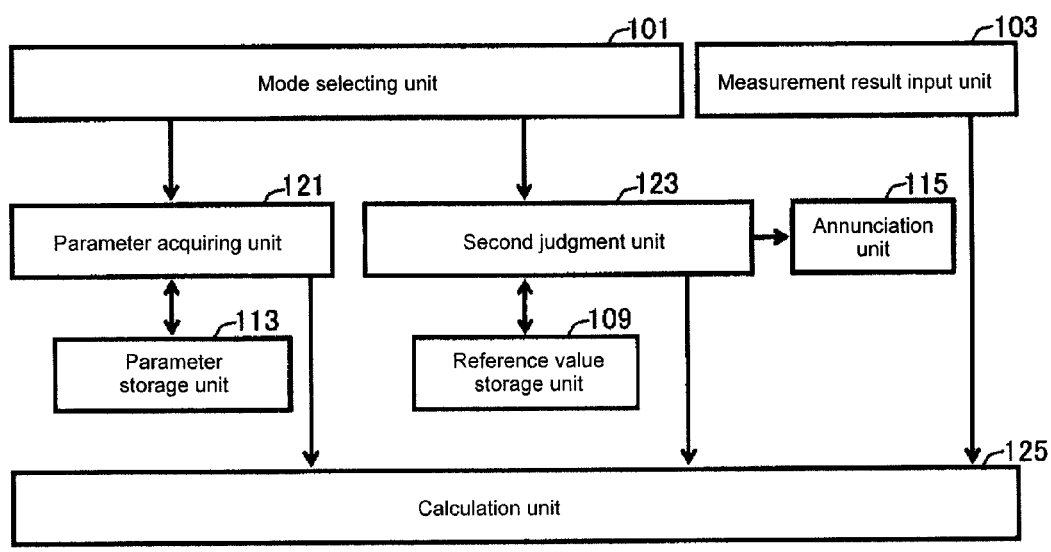
FIG. 9 is a block diagram showing a specific example of the function configuration for performing blood pressure measurement in the sphygmomanometer according to the first embodiment.

In the sphygmomanometer 1, the blood pressure measurement is executed in the without-clothes mode or the with-clothes mode after the registration process is performed. Each function for performing the blood pressure measurement with the sphygmomanometer 1 shown in FIG. 9 is also a function mainly provided in the CPU 40 by having the CPU 40 execute a predetermined program stored in the memory unit 41. Some of the functions shown in FIG. 9 may be provided by other configurations of the CPU 40 shown in FIG. 2.

With reference to FIG. 9, the functions for performing the blood pressure measurement in the sphygmomanometer 1 is configured to include a parameter acquiring unit 121, a second judgment unit 123, and a calculation unit 125, in addition to the mode selecting unit 101, the measurement result input unit 103, the reference value storage unit 109, the parameter storage unit 113, and the annunciation unit 115 shown in FIG. 3.

The mode selecting unit 101 selects the with-clothes mode or the without-clothes mode, and inputs a signal indicating the selection result to the parameter acquiring unit 121 and the second judgment unit 123. The measurement result input unit 103 inputs the measurement result accepted from the pressure sensor 23 through the amplifier 28 and the A/D converter 29 to the second judgment unit 123 and the calculation unit 125.

If the with-clothes mode is selected in the mode selecting unit 101, the parameter acquiring unit 121 acquires the parameters necessary for calculating the blood pressure value when the clothes is worn stored in the parameter storage unit 113 and provides the same to the calculation unit 125.

If the with-clothes mode is selected in the mode selecting unit 101, the second judgment unit 123 compares the reference value in the with-clothes mode stored in the reference value storage unit 109 and the measurement result accepted in the measurement result input unit 103 to judge whether or not the measurement result is within the tolerance level and is appropriate as the measurement result in the with-clothes mode. The amplitude value of the artery blood pressure and the shape of the envelope curve are stored in the reference value storage unit 109 as a reference value in the with-clothes mode. The second judgment unit 123 calculates the amplitude value of the artery blood pressure wave from the measurement result accepted in the measurement result input unit 103, and judges whether or not the difference with the amplitude value or the reference value is within a threshold value. Alternatively, the second judgment unit 123 obtains the shape of the envelope curve from the measurement result accepted in the measurement result input unit 103, and judges whether or not the difference with the shape of the envelope curve or the reference value is within a threshold value. The second judgment unit 123 inputs the signal indicating the judgment result to the calculation unit 125 if judged that the measurement result is the measurement result in the with-clothes mode, and to the annunciation unit 115 if not judged as above. The annunciation unit 115 generates a signal for displaying an error display on the display unit 4, and inputs the same to the display unit 4.

If judged that the measurement result is the measurement result in the with-clothes mode in the second judgment unit 123, the calculation unit 125 computes using the measurement result inputted from the measurement result input unit 103 and the parameter inputted from the parameter acquiring unit 121, and calculates the blood pressure value.

Figure 10:
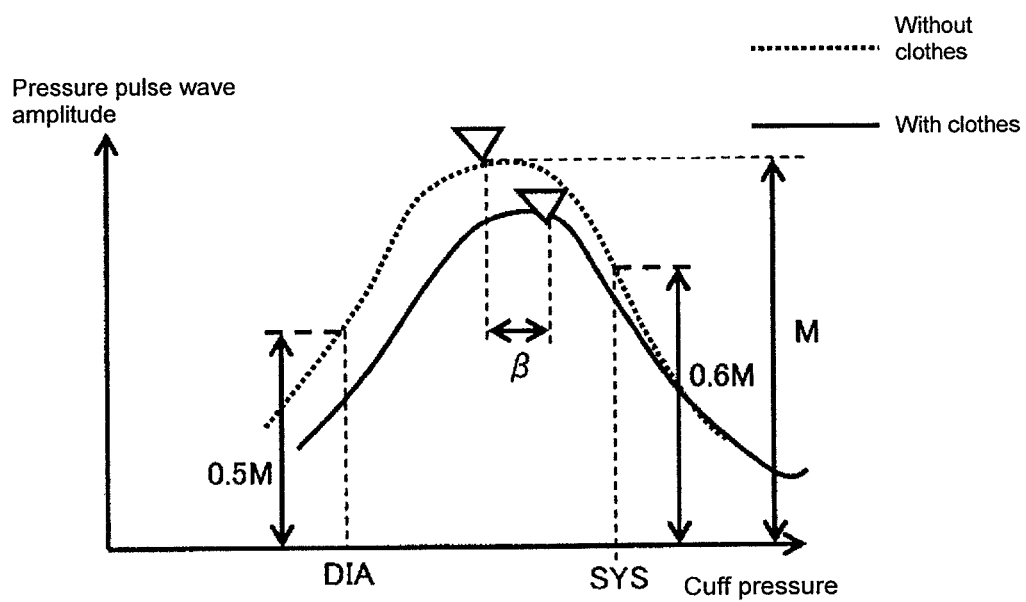
FIG. 10 is a view describing a method of calculating the blood pressure value in the calculation unit 125 of FIG. 9.

FIG. 10 is a view describing a method of calculating the blood pressure value in the calculation unit 125, and is a view showing the curve (envelope curve) showing a change of the amplitude of the artery blood pressure wave with respect to the cuff pressure in the with-clothes mode, and the curve (envelope curve) showing a change of the amplitude of the artery blood pressure wave with respect to the cuff pressure in the without-clothes mode.

Figure 11:
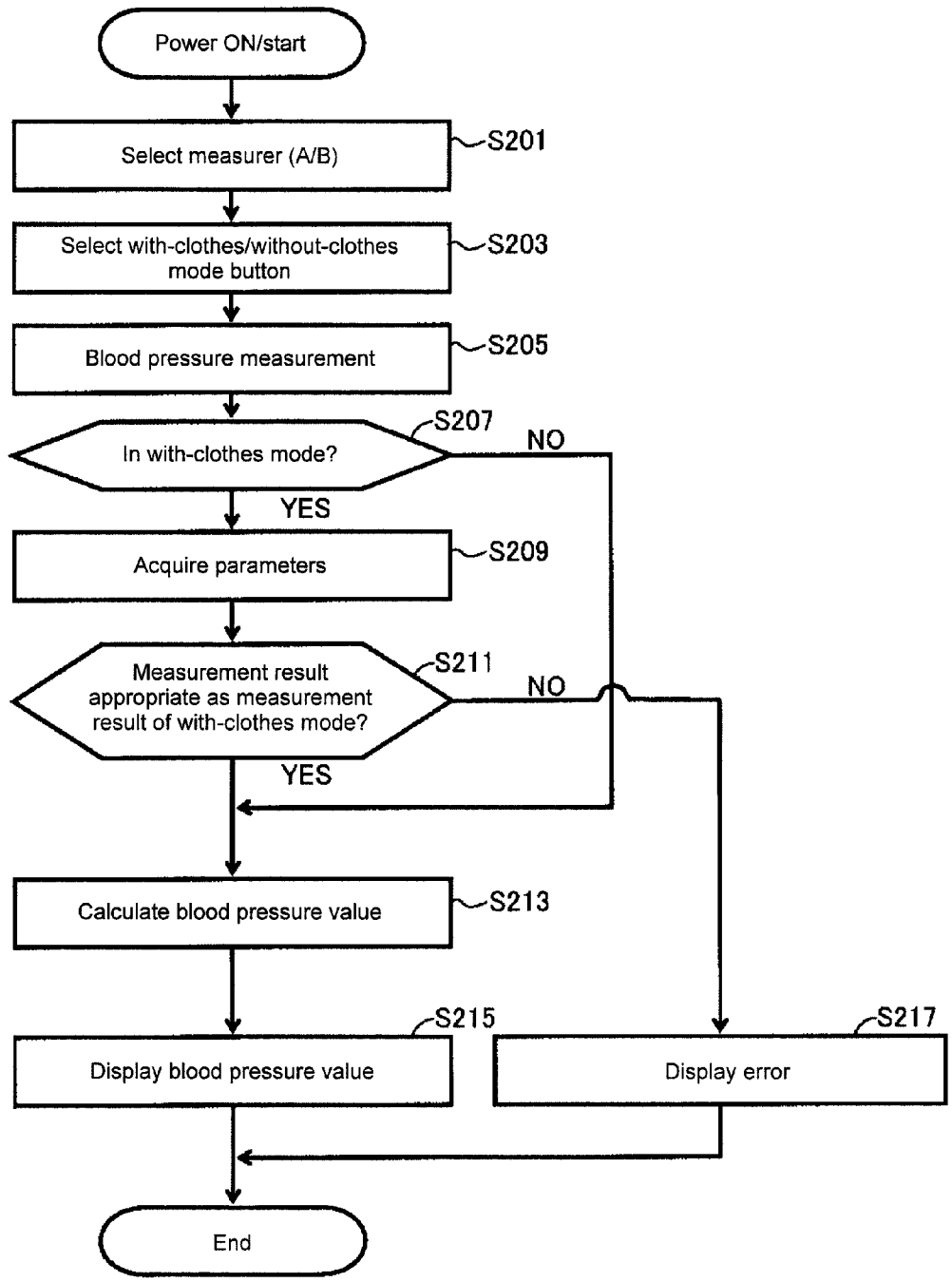
FIG. 11 is a flowchart showing a specific example of a flow of a process in the blood pressure measurement in the sphygmomanometer according to the first embodiment.

A case in which the cardiac systolic blood pressure (SYS) and the cardiac diastolic blood pressure (DIA) are calculated with the cuff pressure that becomes a predetermined proportion of the maximum value of the amplitude of the artery blood pressure wave in the oscillometric method will be described. Assume the cardiac systolic blood pressure is calculated as the cuff pressure that becomes 60% of the maximum value of the amplitude of the artery blood pressure wave, and the cardiac diastolic blood pressure is calculated as the cuff pressure that becomes 50% of the maximum value of the amplitude of the artery blood pressure wave. In this case, with reference to FIG. 10, with the maximum value of the amplitude of the artery blood pressure wave in the without-clothes mode as M, the amplitude (SYS) of the artery blood pressure wave at the cardiac systolic blood pressure and the amplitude (DIA) of the artery blood pressure wave at the cardiac diastolic blood pressure in the without-clothes mode are respectively calculated as, Amplitude (SYS)=0.6M Amplitude (DIA)=0.5M As shown in FIG. 10, the maximum value of the amplitude of the artery blood pressure wave in the with-clothes modes is assumed to be $(1-\alpha 1/M)$ times the maximum value M of the amplitude of the artery blood pressure wave in the without-clothes mode. Assume the cuff pressure at the maximum value of the amplitude of the artery blood pressure wave in the with-clothes mode is transitioned in the negative direction by $\beta 1$ [mmHg] with respect to the cuff pressure at the maximum value of the amplitude of the artery blood pressure wave in the without-clothes mode. In this case, the parameter acquiring unit 121 acquires $\alpha 1$, $\beta 1$ as parameters. The calculation unit 125 uses such parameters to calculate the amplitude (SYS) of the artery blood pressure wave at the cardiac systolic blood pressure and the amplitude (DIA) of the artery blood pressure wave at the cardiac diastolic blood pressure in the with-clothes mode as, Amplitude (SYS)=$0.6M\times(1-\alpha 1/M)-\beta$ Amplitude (DIA)=$0.5M\times(1-\alpha 1/M)-\beta$ The process in blood pressure measurement in the sphygmomanometer 1 shown in the flowchart of FIG. 11 is the process that starts when the button 3-1 is pushed and the power is turned ON. The process of FIG. 11 is realized by having the CPU 40 read out and execute a predetermined program stored in the memory unit 41, and exhibit the functions shown in FIG. 9.

With reference to FIG. 11, the CPU 40 accepts an operation signal for selecting the measurer (A or B) by the operation of the button 3-3 (step S201), and determines the measurer. The CPU 40 then accepts the operation signal for selecting the with-clothes mode or the without-clothes mode by the operation of the button 3-4, and selects the mode in the mode selecting unit 101 (step S203). When the operation signal instructing the start of the blood pressure measurement is inputted by the operation of the button 3-2, the blood pressure measurement is executed, and the measurement result is inputted to the CPU 40 (step S205).

If the with-clothes mode is selected in step S203 (YES in step S207), the parameter acquiring unit 121 acquires the parameters necessary for calculating the blood pressure value when the clothes is worn stored in the parameter storage unit 113 (step S209). If the second judgment unit 123 judges that the measurement result inputted in step S205 is appropriate as the measurement result in the with-clothes mode (YES in step S211), the calculation unit 125 executes the calculation process using the measurement result inputted in step S205 and the parameter acquired in step S209, and calculates the blood pressure value in the with-clothes mode (step S213). The calculated blood pressure value is displayed on the display unit 4 (step S215).

If the second judgment unit 123 judges that the measurement result inputted in step S205 is not appropriate as the measurement result in the with-clothes mode (NO in step S211), the subsequent calculation process is not executed. The annunciation unit 115 generates a signal for displaying an error on the display unit 4, and the error is displayed on the display unit 4 (step S217).

If the without-clothes mode is selected in step S203 (NO in step S207), steps S209, S211 are skipped. The calculation unit 125 executes the calculation process defined in advance using the measurement result inputted in step S205, and calculates the blood pressure value in the without-clothes mode (step S213). The calculation process in step S213 in the without-clothes mode is similar to the calculation process in the case where the blood pressure is normally measured with the clothes off, and is not limited to the specific calculation process in the present invention.

The process of the blood pressure measurement in the sphygmomanometer 1 is thereby terminated.

When the registration process and the blood pressure measurement are performed in the sphygmomanometer 1, the influence of clothes on the measurement result are registered as parameters in advance by comparing the measurement result with clothes on (measurement result in the with-clothes mode) and the measurement result with clothes off (measurement result in the without-clothes mode), and the measurement result in the with-clothes mode is corrected using the parameters to calculate the blood pressure value. Thus, when the blood pressure is measured with clothes on, the influence of clothes is excluded from the obtained measurement result, and the accuracy of the blood pressure value can be enhanced in the same manner as when measured without clothes.

In the first embodiment, the button 3-4 is arranged on the sphygmomanometer 1, and the user such as the measurer selects whether to measure with clothes on or to measure with clothes off. In the sphygmomanometer 1, however, whether the measurement result measured with clothes on or the measurement result measured with clothes off may be automatically judged by comparing the measurement result with the reference value. In other words, whether the measurement result is in the with-clothes mode or the measurement result is in the without-clothes mode may be judged by comparing with the reference value in the with-clothes mode for all the measurement results in step S211 without performing the processes of steps S203, S207, and the blood pressure value may be calculated according to the result. The parameter setting may be provided for each user. As assumed that the blood pressure is measured with the same clothes such as a pajama before and after sleeping, enlightenment effect in measuring the blood pressure at the same time and in the same state can be naturally expected.

[Second Embodiment]

In the second embodiment, the information related to the attribute of the clothes is set as the information related to clothes in time of measurement of the person to be measured. In the subsequent specific examples, the mode is set with the thickness of the fabric of the clothes as the attribute of the clothes. However, the attribute of the clothes is not limited to the thickness of the fabric, and may be other attributes that influence the measurement result such as the design of the area related to the measurement site, the number of clothes, and the like.

Figure 12:
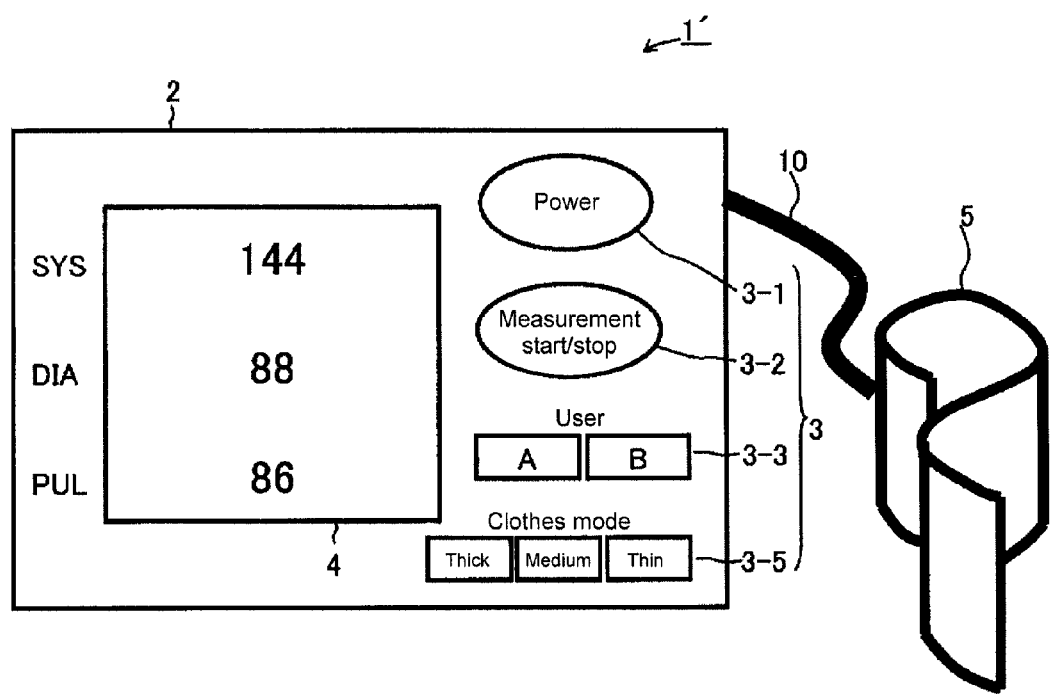
FIG. 12 is a schematic view of an outer appearance view of a sphygmomanometer according to a second embodiment of the blood pressure measurement device.

With reference to FIG. 12, in the sphygmomanometer 1' according to the second embodiment of the blood pressure measurement device, the operation unit 3 includes a button 3-5 for selecting the type of clothes in place of the button 3-4 of the sphygmomanometer 1 according to the first embodiment. Specifically, a button for selecting whether the fabric of the clothes is thick, thin, or medium is arranged.

In the sphygmomanometer 1', the registration process similar to the registration process shown in FIG. 8 is executed, and the reference value and the parameters are registered for every attribute of the clothes, that is, for every thickness of the fabric. In the subsequent description, the with-clothes mode in the case where the fabric of the clothes is thick is referred to as "thick mode", the with-clothes mode in the case where the fabric is thin is referred to as "thin mode", and the with-clothes mode in the case where the thickness of the fabric is intermediate is referred to as "middle mode". In the specific example, the type of thickness of the fabric of the clothes is the above-described three types, but may be two types or may be four or more types. In such cases as well, process is performed similar to the subsequent description.

Figure 13:
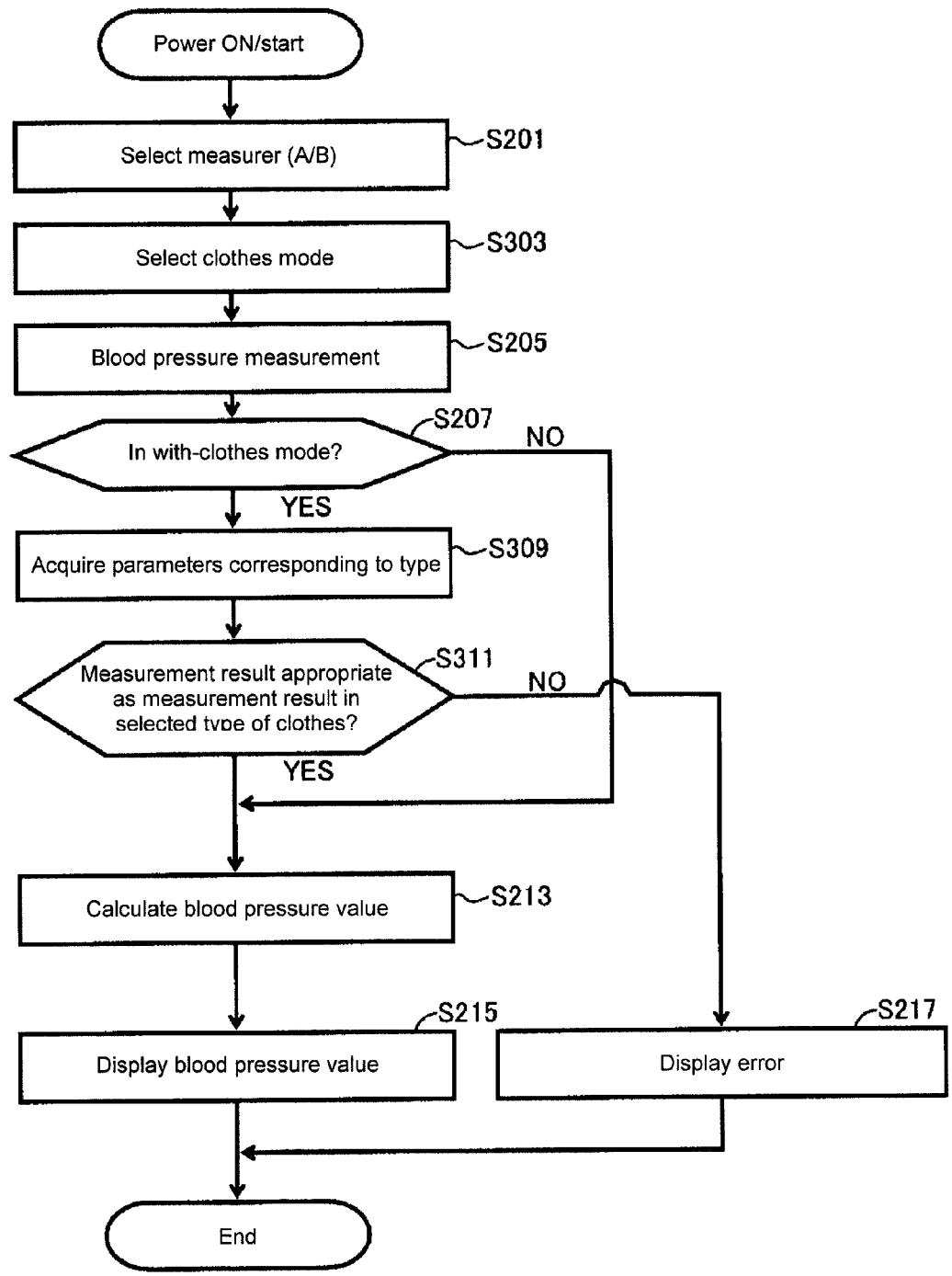
FIG. 13 is a flowchart showing a specific example of a flow of a process in the blood pressure measurement in the sphygmomanometer according to the second embodiment.
Figure 14:
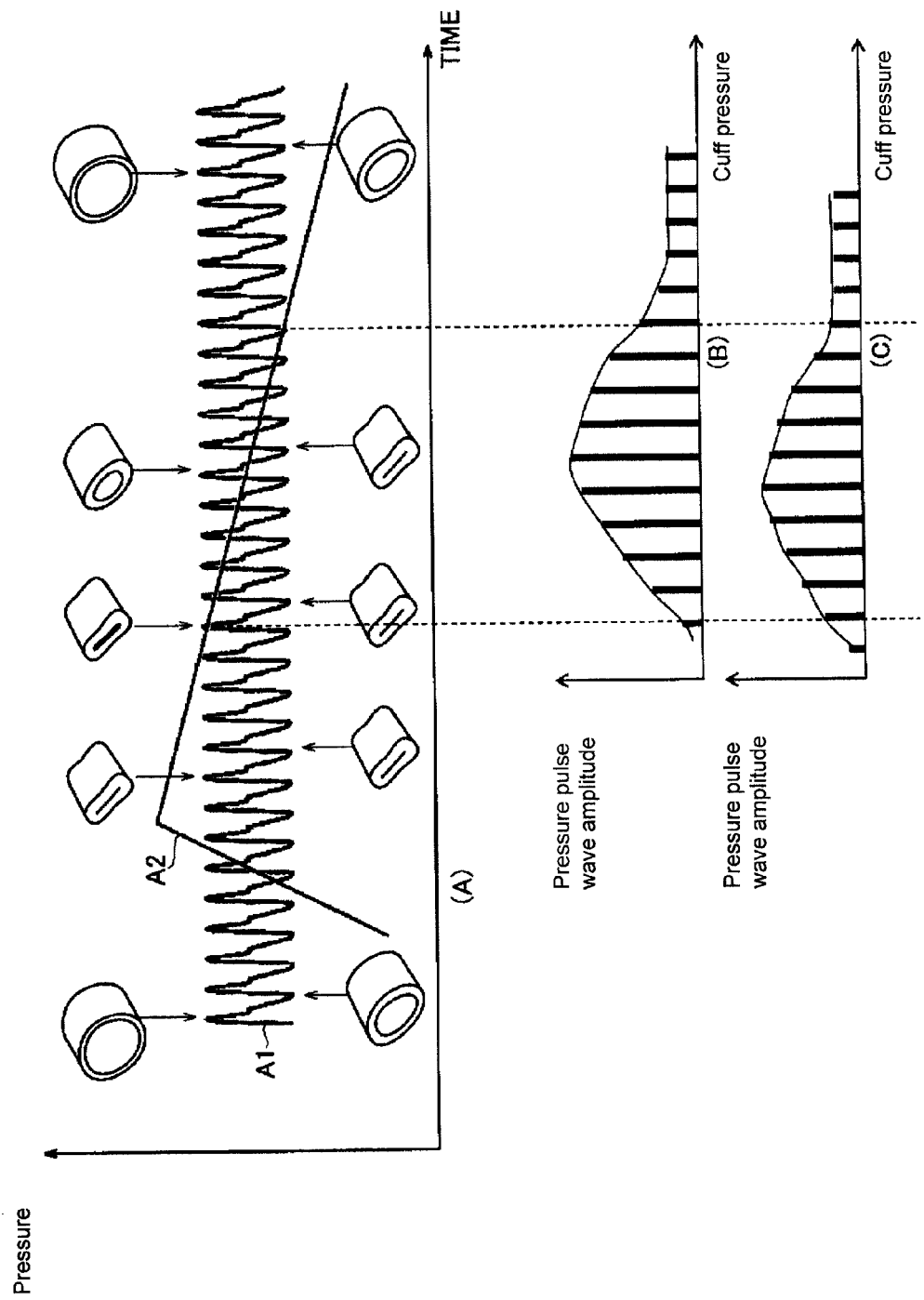
FIG. 14 is a view describing a determination method of a blood pressure value in an oscillometric method.

The process in blood pressure measurement in the sphygmomanometer 1' shown in the flowchart of FIG. 13 is also the process that starts when the button 3-1 is pushed and the power is turned ON. The process of FIG. 13 is realized by having the CPU 40 read out and execute a predetermined program stored in the memory unit 41, and exhibit the functions shown in FIG. 9.

With reference to FIG. 13, the CPU 40 accepts the operation signal for selecting the measurer (A or B) by the operation of the button 3-3 (step S201), and determines the measurer. In place of the process of step S203, the CPU 40 accepts the operation signal for selecting the with-clothes mode or the without-clothes mode, and furthermore, the thick mode, the middle mode, or the thin mode in the with-clothes mode by the operation of the button 3-5, and selects the mode in the mode selecting unit 101 in the sphygmomanometer 1' (step S303). When the operation signal instructing the start of the blood pressure measurement is inputted by the operation of the button 3-2, the blood pressure measurement is executed, and the measurement result is inputted to the CPU 40 (step S205).

When the with-clothes mode is selected in step S303 (YES in step S207), in the sphygmomanometer 1', the parameters corresponding to the thick mode, the thin mode, and the middle mode of the with-clothes mode selected in step S303 of the parameters necessary for calculating the blood pressure value in the case where the clothes is worn stored in the parameter storage unit 113 are acquired in the parameter acquiring unit 121 (step S309). In step S311, the second judgment unit 123 judges whether or not the measurement result inputted in step S205 is appropriate as the measurement result in the thick mode, the thin mode or the middle mode of with-clothes mode of the with-clothes mode selected in step S303 by comparing with the reference value in each mode stored in the reference value storage unit 109. If the second judgment unit 123 judges as appropriate (YES in step S311), the calculation unit 125 executes the calculation process using the measurement result inputted in step S205 and the parameters acquired in step S309, and calculates the blood pressure value in the with-clothes mode (step S213). The calculated blood pressure value is displayed on the display unit 4 (step S215).

If the second judgment unit 123 judges that the measurement result inputted in step S205 is not appropriate as the measurement result in the with-clothes mode (NO in step S211), the subsequent calculation process is not executed. The annunciation unit 115 generates a signal for displaying an error on the display unit 4, and the error is displayed on the display unit 4 (step S217). In the sphygmomanometer 1', an error of a content annunciating that there is a possibility of not being the mode corresponding to the selected attribute of the clothes of the with-clothes mode may be displayed. In this case, the blood pressure value is calculated using the parameters corresponding to the mode selected in step S213 while displaying the error in step S217, and the calculated blood pressure value may be displayed with the error display in step S215.

If the without-clothes mode is selected in step S303 (NO in step S207), steps S309, S311 are skipped. The calculation unit 125 executes the calculation process defined in advance using the measurement result inputted in step S205, and calculates the blood pressure value in the without-clothes mode (step S213). The calculation process in step S213 in the without-clothes mode is similar to the calculation process in the case where the blood pressure is normally measured with the clothes off, and is not limited to the specific calculation process in the present invention.

The process of the blood pressure measurement in the sphygmomanometer 1' is thereby terminated.

In the case where the fabric of the clothes is thick (thick mode), the loss of the pulse beat and the compression force of the cuff due to the clothes is large compared to when the fabric is thin (thin mode). In the sphygmomanometer 1', the parameters that take into consideration the attribute of such clothes are registered and used for the calculation of the blood pressure value. Thus, the measurement accuracy in the case where the blood pressure is measured with clothes on can be further enhanced by using the sphygmomanometer 1'.

Note that the sphygmomanometer 1' may also be configured to automatically judge the with-clothes mode/without-clothes mode, and furthermore, the mode corresponding to the attribute of the clothes by comparing the measurement result with the reference value corresponding to the attribute of the clothes.

In FIGS. 1 and 12, the sphygmomanometer is a type in which the armband 5 is made of a soft raw material such as cloth and is wrapped around the upper arm or the measurement site. However, the sphygmomanometer 1, 1' is not limited to such a configuration, and the armband 5 may be a fixed type.

As another embodiment, the sphygmomanometer 1 may be connected to a computer such as a personal computer, at least the first judgment unit 107, the reference value storage unit 109, the parameter determination unit 111, and the parameter storage unit 113 of the functions shown in FIG. 3 may be included in the computer, and the registration process may be executed in the computer that acquired the measurement result and the information related to the selected mode from the sphygmomanometer 1. Similarly, at least the parameter acquiring unit 121, the second judgment unit 123, and the calculation unit 125 of the functions shown in FIG. 9 may be included in the computer, and the process of calculating the blood pressure value from the measurement result may be executed in the computer that acquired the measurement result and the information related to the selected mode from the sphygmomanometer 1. Furthermore, in the computer, the selection of the mode may be accepted, and the registration process and/or the process of calculating the blood pressure value from the measurement result may be executed using the measurement result acquired from the sphygmomanometer 1. Moreover, the computer may be connected to another device such as a server, the reference value storage unit 109, the parameter storage unit 113, and the like may be arranged in the another device, and the computer may execute the above-described processes by acquiring the reference value and the parameters from the another device, as necessary.

A program for causing the computer to execute the registration process and/or the process of calculating the blood pressure value from the measurement result may be provided. Such a program may be provided as a program product by being recorded in a computer readable recording medium such as a flexible disc, a CD-ROM (Compact Disk-Read Only Memory), a ROM (Read Only Memory), a RAM (Random Access Memory), a memory card and the like to be attached to the computer. Alternatively, the program may be provided by being recorded in a recording medium such as a hard disk built in the computer. The program may also be provided by being downloaded through the network.

The program according to the present invention may call out the necessary module, of the program modules provided as part of the operating system (OS) of the computer, in a predetermined array at a predetermined timing and cause the module to execute the process. In this case, the program itself does not include the module, and the process is executed in cooperation with the OS. The program that does not include such a module is also encompassed in the program according to the present invention.

The program according to the present invention may be provided by being incorporated in part of another program. In this case as well, the program itself does not include the module included in the another program, and the process is executed in cooperation with the another program. The program incorporated in the another program is also encompassed in the program according to the present invention.

The program product to be provided is installed in a program storage unit such as a hard disk, and then executed. The program product includes the program itself and the recording medium on which the program is recorded.

The embodiments disclosed herein are illustrative in all aspects and should not be construed as being restrictive. The scope of the invention is defined by the claims rather than by the description made above, and the explanation equivalent to the claims and all modifications within the claims are to be encompassed.

The invention claimed is:

1. A blood pressure measurement device comprising:
a measurement fluid bag;
a sensor that measures a change in inner pressure of the measurement fluid bag;
a first setting unit that sets a parameter in correspondence to information related to clothing at a measurement site at a time of measurement of a person to be measured;
a calculation unit that calculates a blood pressure value using the parameter and based on the change in inner pressure of the measurement fluid bag obtained by the sensor; and
a second setting unit that allows a user to manually select and set information related to clothing at the measurement site at the time of the measurement of the person to be measured.

2. The blood pressure measurement device according to claim 1, wherein the information related to clothing at the measurement site at the time of the measurement of the person to be measured is whether the person to be measured is clothed at the measurement site at the time of the measurement.

3. The blood pressure measurement device according to claim 1, wherein the information related to clothing at the measurement site at the time of the measurement of the person to be measured is information related to an attribute of the clothes the person to be measured is wearing at the measurement site at the time of measurement.

4. The blood pressure measurement device according to claim 1, further comprising:
a storage unit that stores the parameter;
wherein the first setting unit includes an acquiring unit that acquires the parameter corresponding to the information related to the clothing at the measurement site at the time of the measurement of the person to be measured from the storage unit.

5. The blood pressure measurement device according to claim 1, further comprising:
a determination unit that determines the parameter corresponding to the information related to the clothes at the time of the measurement of the person to be measured using a change in inner pressure of the measurement fluid bag obtained by the sensor at the measurement site.

6. The blood pressure measurement device according to claim 1, further comprising:
   a judgment unit that judges whether or not to calculate the blood pressure value using the parameter and using a reference value corresponding to the information related to the clothing at the measurement site at the time of the measurement of the person to be measured and the change in inner pressure of the measurement fluid bag obtained by the sensor.

7. A processing method in a computer of measurement data obtained by a blood pressure measurement device including a measurement fluid bag and a sensor for measuring a change in inner pressure of the measurement fluid bag, the method comprising:
   setting a parameter in correspondence to information related to clothing at a measurement site at the time of measurement of a person to be measured;
   calculating, using a processor in the computer, a blood pressure value using the parameter based on the change in inner pressure of the measurement fluid bag obtained by the sensor; and
   allowing a user to manually select and set information related to clothing at the measurement site at the time of the measurement of the person to be measured.

8. A non-transitory computer readable medium comprising instructions that, when executed, cause a computer to perform processing of measurement data obtained by a blood pressure measurement device including a measurement fluid bag and a sensor for measuring a change in inner pressure of the measurement fluid bag, the processing comprising:
   setting a parameter in correspondence to information related to clothing at a measurement site at the time of measurement of a person to be measured;
   calculating a blood pressure value using the parameter based on the change in inner pressure of the measurement fluid bag obtained by the sensor; and
   allowing a user to manually select and set information related to clothing at the measurement site at the time of the measurement of the person to be measured.

* * * * *